United States Patent
Park et al.

(10) Patent No.: US 12,404,234 B2
(45) Date of Patent: Sep. 2, 2025

(54) METHOD OF PRODUCING ACRYLONITRILE DIMER

(71) Applicant: LG CHEM, LTD., Seoul (KR)

(72) Inventors: Sae Hume Park, Daejeon (KR); Ji Ha Kim, Daejeon (KR); Yu Jin An, Daejeon (KR); Wan Kyu Oh, Daejeon (KR); Hyun Chul Jung, Daejeon (KR); Jeong Heon Ahn, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1150 days.

(21) Appl. No.: 17/292,951

(22) PCT Filed: Oct. 14, 2020

(86) PCT No.: PCT/KR2020/013977
§ 371 (c)(1),
(2) Date: May 11, 2021

(87) PCT Pub. No.: WO2021/096075
PCT Pub. Date: May 20, 2021

(65) Prior Publication Data
US 2022/0306571 A1    Sep. 29, 2022

(30) Foreign Application Priority Data

Nov. 11, 2019  (KR) .................. 10-2019-0143198
Sep. 28, 2020  (KR) .................. 10-2020-0125786

(51) Int. Cl.
*C07C 253/30*   (2006.01)
*C07C 253/34*   (2006.01)

(52) U.S. Cl.
CPC .......... *C07C 253/30* (2013.01); *C07C 253/34* (2013.01)

(58) Field of Classification Search
CPC ........................... C07C 253/30; C07C 253/34
See application file for complete search history.

(56) References Cited

U.S. PATENT DOCUMENTS

| | | |
|---|---|---|
| 3,732,281 A | 5/1973 | Feldman et al. |
| 4,102,915 A | 7/1978 | Jennings |
| 4,126,632 A | 11/1978 | Hogan et al. |
| 4,316,857 A | 2/1982 | Gilbert |
| 4,422,981 A | 12/1983 | Omori |
| 4,639,539 A | 1/1987 | Hovey |
| 4,952,541 A | 8/1990 | Heckle |

FOREIGN PATENT DOCUMENTS

| | | |
|---|---|---|
| EP | 0010886 B1 | 12/1982 |
| EP | 0187132 B1 | 10/1988 |
| JP | 2888392 B2 | 2/1999 |
| KR | 10-0374680 B1 | 3/2003 |

*Primary Examiner* — Alicia L Otton
(74) *Attorney, Agent, or Firm* — BRYAN CAVE LEIGHTON PAISNER LLP

(57) ABSTRACT

The present invention relates to a method of producing an acrylonitrile dimer, the method including: feeding an acrylonitrile monomer, a nonpolar solvent, an alcohol solvent, and a phosphorus-based catalyst to a dimerization reactor to perform a dimerization reaction and reaction product to a distillation column; feeding the acrylonitrile monomer, the nonpolar solvent, and the alcohol solvent from the distillation column to the dimerization reactor; feeding an acrylonitrile dimer and the phosphorus-based catalyst from the distillation column to an extraction device; oxidizing the phosphorus-based catalyst by feeding water including an acid component to the extraction device to inactivate the phosphorus-based catalyst; and separating the inactivated phosphorus-based catalyst and the acrylonitrile dimer.

13 Claims, 1 Drawing Sheet

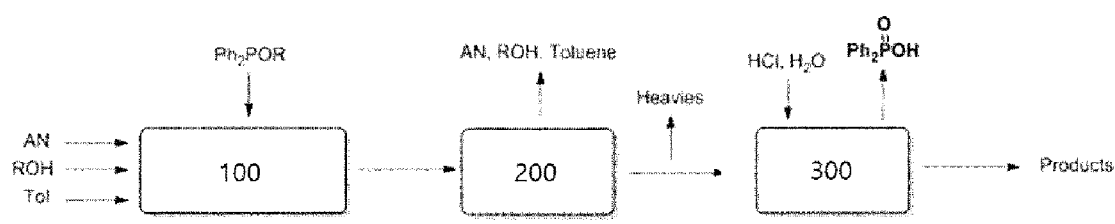

METHOD OF PRODUCING ACRYLONITRILE DIMER

The present application is a National Phase entry pursuant to 35 U.S.C § 371 of International Application No. PCT/KR2020/013977 filed on Oct. 14, 2020, and claims priority to and the benefit of Korean Patent Application No. 10-2019-0143198, filed on Nov. 11, 2019, and Korean Patent Application No. 10-2020-0125786, filed on Sep. 28, 2020, the entire contents of which are incorporated herein by reference.

FIELD

The present invention relates to a method of producing an acrylonitrile dimer, and more particularly, to a method of producing acrylonitrile at a high yield by efficiently separating a phosphorus-based catalyst in an acrylonitrile dimerization reaction.

BACKGROUND

A dimerization reaction of acrylonitrile (AN) is a process of allowing an acrylonitrile monomer to react in a solvent including a proton donating solvent such as isopropyl alcohol (IPA) and an inert solvent such as toluene (TOL) in the presence of a catalyst to dimerize the acrylonitrile monomer.

Studies have been conventionally conducted to separate a catalyst from a reaction product including an acrylonitrile dimer, an unreacted acrylonitrile monomer, isopropyl alcohol, toluene, and the catalyst after the acrylonitrile dimerization reaction by a distillation method or a liquid-liquid extraction (LLE) method.

Specifically, the distillation method is a method of separating the catalyst by applying heat using characteristics of a phosphorus-based catalyst having a boiling point higher than that of the reaction product. In a case where the catalyst is separated from the acrylonitrile dimerization reaction product by the distillation method, a side reaction of acrylonitrile dimerization products proceeds due to heat, and an acrylonitrile trimer, multimer, and the like, are thus produced, such that yield of the acrylonitrile dimer is reduced.

In addition, the LLE method is a method of separating the unreacted acrylonitrile monomer, isopropyl alcohol, and toluene from the reaction product including acrylonitrile dimer, unreacted acrylonitrile monomer, isopropyl alcohol, toluene, and the catalyst through distillation, reusing the unreacted acrylonitrile monomer, isopropyl alcohol, and toluene in the acrylonitrile dimerization reaction, feeding a separate organic solvent for dissolving the catalyst in a mixture including the acrylonitrile dimer and the catalyst to extract the catalyst, and then reusing the catalyst in the acrylonitrile dimerization reaction. In a case where the catalyst is separated from the acrylonitrile dimerization reaction product by the LLE method, it is difficult to select a solvent having a high dissolution rate for a catalyst.

Therefore, studies are required to on a method of simply separating the catalyst from the acrylonitrile dimerization reaction product and reusing the catalyst.

SUMMARY

In order to solve the problems mentioned in the background, an object of the present invention is to provide a method of producing an acrylonitrile dimer at a high yield by separating a phosphorus-based catalyst from an acrylonitrile dimerization reaction product by a simple method.

That is, in the present invention, an unreacted acrylonitrile monomer and an alcohol solvent are separated from an acrylonitrile dimerization reaction product including an acrylonitrile dimer, unreacted acrylonitrile monomer, a nonpolar solvent, an alcohol solvent, and a phosphorus-based catalyst, through distillation first, the unreacted acrylonitrile monomer and the alcohol solvent are circulated to a dimerization reactor, water including an acid are mixed with a remaining mixture including the acrylonitrile dimer, the nonpolar solvent, and the phosphorus-based catalyst to solidify the phosphorus-based catalyst, and then, the solidified phosphorus-based catalyst may be separated by a simple method using a filter.

In one general aspect, a method of producing an acrylonitrile dimer includes: feeding an acrylonitrile monomer, a nonpolar solvent, an alcohol solvent, and a phosphorus-based catalyst to a dimerization reactor to perform a dimerization reaction and feeding a reaction product to a distillation column; feeding the acrylonitrile monomer, the nonpolar solvent, and the alcohol solvent partially or entirely separated from the distillation column to the dimerization reactor; feeding an acrylonitrile dimer and the phosphorus-based catalyst separated from the distillation column to an extraction device; oxidizing the phosphorus-based catalyst by feeding water including an acid component to the extraction device to inactivate the phosphorus-based catalyst; and separating the inactivated phosphorus-based catalyst from the acrylonitrile dimer.

According to the method of producing an acrylonitrile dimer of the present invention, the unreacted acrylonitrile monomer, the alcohol solvent, and the nonpolar solvent are partially or entirely separated from the acrylonitrile dimerization reaction product including the acrylonitrile dimer, the unreacted acrylonitrile monomer, the nonpolar solvent, the alcohol solvent, and the phosphorus-based catalyst through distillation first, the water including the acid component is mixed with the acrylonitrile dimer and the phosphorus-based catalyst to solidify the phosphorus-based catalyst, and then, the solidified phosphorus-based catalyst may be separated by a simple and efficient method using a filter.

In addition, water is used as a solvent for separating the phosphorus-based catalyst, such that cost may be reduced.

In addition, the acrylonitrile dimer is separated at a high purity, such that quality of the acrylonitrile dimer may be improved.

BRIEF DESCRIPTION OF THE DRAWING

FIG. 1 is a process flow diagram of a method of producing an acrylonitrile dimer according to an exemplary embodiment of the present invention.

DETAILED DESCRIPTION

The terms and words used in the description and claims of the present invention are not to be construed as general or dictionary meanings but are to be construed as meanings and concepts meeting the technical ideas of the present invention based on a principle that the inventors can appropriately define the concepts of terms in order to describe their own inventions in the best mode.

Hereinafter, the present invention will be described in more detail with reference to FIG. 1 in order to assist in the understanding of the present invention.

According to the present invention, a method of producing an acrylonitrile dimer is provided including: feeding an acrylonitrile monomer, a nonpolar solvent, an alcohol solvent, and a phosphorus-based catalyst to a dimerization reactor to perform a dimerization reaction and feeding a reaction product to a distillation column; feeding the acrylonitrile monomer, the nonpolar solvent, and the alcohol solvent partially or entirely separated from the distillation column to the dimerization reactor; feeding an acrylonitrile dimer and the phosphorus-based catalyst separated from the distillation column to an extraction device; oxidizing the phosphorus-based catalyst by feeding water including an acid component to the extraction device to inactivate the phosphorus-based catalyst; and separating the inactivated phosphorus-based catalyst from the acrylonitrile dimer.

According to an exemplary embodiment of the present invention, in a step for producing the acrylonitrile dimer, a raw material component, a product, and the like may be transferred in a stream state. The "stream" may refer to a flow of a fluid in a process and may also refer to a fluid itself flowing through a pipe. Specifically, the "stream" may refer to both a fluid itself flowing through a pipe connecting respective apparatuses and a flow of the fluid. In addition, the fluid may refer to gas or liquid.

The dimerization reaction of acrylonitrile (AN) is a process of allowing an acrylonitrile monomer to react in a solvent in the presence of a catalyst to dimerize the acrylonitrile monomer.

Studies have been conventionally conducted to separate a catalyst from a reaction product including an acrylonitrile dimer, an unreacted acrylonitrile monomer, isopropyl alcohol, toluene, and the catalyst after the reaction in the acrylonitrile dimerization reaction by a distillation method or a liquid-liquid extraction (LLE) method using an organic solvent.

However, in a case where the catalyst is separated from the acrylonitrile dimerization reaction product by the distillation method, a side reaction of acrylonitrile dimerization products proceeds, and an acrylonitrile trimer, multimer, and the like are thus produced, such that a yield of the acrylonitrile dimer is reduced. In a case where the catalyst is separated from the acrylonitrile dimerization reaction product by the LLE method, it is difficult to select a solvent having a high dissolution rate for a catalyst.

Therefore, the present invention is to provide a method of simply separating a catalyst from an acrylonitrile dimerization reaction product at a low cost, and reusing the catalyst.

According to an exemplary embodiment of the present invention, the acrylonitrile dimerization reaction may be performed by a method of feeding the acrylonitrile monomer, the nonpolar solvent, the alcohol solvent, and the phosphorus-based catalyst to a dimerization reactor 100 (FIG. 1) to perform a dimerization reaction.

According to an exemplary embodiment of the present invention, the acrylonitrile dimerization reaction may be performed by a general method known in the art. For example, the acrylonitrile dimerization reaction may be performed by feeding adequate amounts of the acrylonitrile monomer, the nonpolar solvent, the alcohol solvent, and the phosphorus-based catalyst to the dimerization reactor 100 in an optimum temperature range and pressure range.

According to an exemplary embodiment of the present invention, in the acrylonitrile dimerization reaction, the nonpolar solvent, the alcohol solvent, and the phosphorus-based catalyst may be fed to the dimerization reactor 100 in a volume ratio of about 10:3:1, but the present invention is not limited thereto.

According to an exemplary embodiment of the present invention, the acrylonitrile dimerization reaction may be performed at a temperature of 0° C. to 100° C., 0° C. to 80° C., or 0° C. to 60° C., and at a pressure of 1 bar to 5 bar, 1 bar to bar, or 1 bar to 3 bar. When the acrylonitrile dimerization reaction is performed within the above temperature and pressure ranges, an acrylonitrile dimer may be produced at an excellent conversion rate.

According to an exemplary embodiment of the present invention, the nonpolar solvent fed to the dimerization reactor 100 may include, for example, one or more selected from the group consisting of toluene, chlorobenzene, benzene, dichloromethane, and 1,4-dioxane. As a specific example, the nonpolar solvent may be toluene.

According to an exemplary embodiment of the present invention, the alcohol solvent fed to the dimerization reactor 100 may include, for example, one or more selected from the group consisting of isopropyl alcohol, methyl alcohol, and cyclohexane alcohol. As a specific example, the alcohol solvent may be isopropyl alcohol.

According to an exemplary embodiment of the present invention, the phosphorus-based catalyst fed to the dimerization reactor 100 may be represented by Formula 1.

[Formula 1]

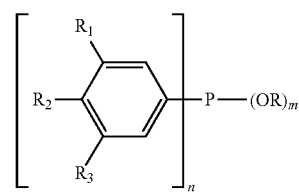

In Formula 1,

R represents an alkyl group having 1 to 5 carbon atoms, an aryl group having 6 to 12 carbon atoms, or a cycloalkyl group having 1 to 8 carbon atoms, each of $R_1$ to $R_3$ represents hydrogen, or an alkyl group, amine group, or alkoxy group having 1 to 5 carbon atoms, and n and m are each independently an integer of 1 or 2.

As a specific example, the phosphorus-based catalyst may be represented by Formula 1-1.

[Formula 1-1]

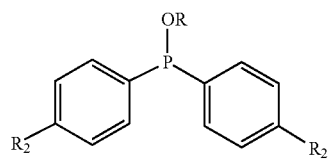

In Formula 1-1,

R is a methyl group, an ethyl group, an isopropyl group, or a cyclohexyl group, and $R_2$ is hydrogen, a methyl group, or an ethyl group.

As a more specific example, the phosphorus-based catalyst may be represented by Formula 1-2.

[Formula 1-2]

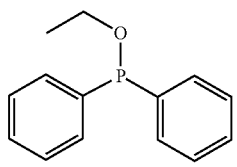

According to an exemplary embodiment of the present invention, an acrylonitrile dimer may be produced by subjecting the acrylonitrile monomer to a dimerization reaction in the presence of the nonpolar solvent, the alcohol solvent, and the phosphorus-based catalyst in the dimerization reactor 100. Specifically, the reaction product obtained by the acrylonitrile dimerization reaction may include an acrylonitrile dimer, an unreacted acrylonitrile monomer, a nonpolar solvent, an alcohol solvent, a phosphorus-based catalyst, and heavies.

According to an exemplary embodiment of the present invention, the reaction product obtained by the dimerization reaction may be fed to a distillation column 200.

The distillation column 200 is used to separate the unreacted acrylonitrile monomer, the alcohol solvent, and the nonpolar solvent from the reaction product obtained by the dimerization reaction. Specifically, the reaction product obtained by the dimerization reaction may be fed to the distillation column 200, the acrylonitrile monomer, the nonpolar solvent, and the alcohol solvent may be circulated from the distillation column 200 to the dimerization reactor 100, and the acrylonitrile dimer and the phosphorus-based catalyst may be fed to an extraction device 300.

In this case, the nonpolar solvent in the reaction product obtained by the dimerization reaction may be partially or entirely circulated from the distillation column 200 to the dimerization reactor 100, or may be partially or entirely fed from the distillation column 200 to the extraction device 300.

A content of the alcohol solvent in the extraction device 300 may be 1 wt % or less. For example, the content of the alcohol solvent in the extraction device 300 may be 0.001 wt % to 1 wt %, 0.1 wt % to 1 wt %, or 0.5 wt % to 1 wt %, and may preferably be close to 0 wt %. By controlling the content of the alcohol solvent in the extraction device 300 within the above ranges, it is easy to solidify and separate the phosphorus-based catalyst in a step described below.

As a specific example, in order to separate the phosphorus-based catalyst from the mixture of the acrylonitrile dimer and the phosphorus-based catalyst fed to the extraction device 300, the phosphorus-based catalyst may be solidified by oxidation and inactivation and then the phosphorus-based catalyst in a solid state may be separated in a step described below. However, in this case, in a case where the alcohol solvent is mixed in the mixture of the acrylonitrile dimer and the phosphorus-based catalyst, the phosphorus-based catalyst solidified by the oxidation and inactivation is re-dissolved in the alcohol solvent, such that it may be difficult to separate the phosphorus-based catalyst by solidification.

That is, in order to separate the phosphorus-based catalyst from the reaction product obtained by the dimerization reaction, as described above, the alcohol solvent is preferentially separated from the reaction product obtained by the dimerization reaction, and the phosphorus-based catalyst in the reaction product from which the alcohol solvent is separated is solidified by oxidation and inactivation in a step described below, such that the phosphorus-based catalyst in the solid state may be easily separated.

A content of the nonpolar solvent in the extraction device 300 may be 5 wt % or less. For example, the content of the nonpolar solvent in the extraction device 300 may be 0.001 wt % to 5 wt %, 0.001 wt % to 3 wt %, or 0.5 wt % to 1 wt %, and may preferably be close to 0 wt %. By controlling the content of the nonpolar solvent in the extraction device 300 within the above ranges, a separation process of the solidified phosphorus-based catalyst using a filter may be easily performed in a step described below.

As a specific example, even when the nonpolar solvent is mixed in the mixture of the acrylonitrile dimer and the phosphorus-based catalyst, from which the alcohol solvent is separated, the phosphorus-based catalyst solidified by oxidation and inactivation is not re-dissolved in a step described below, such that the phosphorus-based catalyst in the solid state may be easily separated.

That is, the alcohol solvent in the mixture including the phosphorus-based catalyst is required to be separated in advance of the solidification process of the phosphorus-based catalyst by oxidation and inactivation, but the solidified phosphorus-based catalyst may be easily separated by oxidation and inactivation even when the nonpolar solvent is present in the mixture including the phosphorus-based catalyst.

An operation temperature of the distillation column 200 may be 40° C. to 150° C. For example, the operation temperature of the distillation column 200 may be 50° C. to 150° C., 50° C. to 120° C., or 80° C. to 120° C. In addition, an operation pressure of the distillation column 200 may be 0.001 bar to 3 bar. For example, the operation pressure of the distillation column 200 may be 0.001 bar to 2 bar, 0.01 bar to 2 bar, or 0.01 bar to 1.5 bar. By controlling the operation temperature and the operation pressure of the distillation column 200 within the above ranges, the unreacted acrylonitrile monomer, the alcohol solvent, and the nonpolar solvent may be partially or entirely separated through a top of the distillation column 200 and the acrylonitrile dimer and the phosphorus-based catalyst may be efficiently separated through a bottom of the distillation column 200, without distillation of the acrylonitrile dimer and the phosphorus-based catalyst.

The heavies may be included in components separated through the bottom of the distillation column 200. Therefore, the heavies may be removed using a filter before being fed to the extraction device 300. For example, the heavies may include an acrylonitrile polymer, a solid by-product, and the like.

According to an exemplary embodiment of the present invention, the extraction device 300 may be used to separate the phosphorus-based catalyst from the mixture including the acrylonitrile dimer, the nonpolar solvent, and the phosphorus-based catalyst.

Water including an acid component may be fed to the extraction device 300. In a case where the water including the acid component and the phosphorus-based catalyst are mixed with each other, the phosphorus-based catalyst may be oxidized and may thus be inactivated.

The water including the acid component may be fed to the extraction device 300 in an amount of 2 equivalents or more, with respect to the phosphorus-based catalyst. For example, the water including the acid component may be fed to the extraction device 300 in an amount of 2 equivalents to 5 equivalents, 2 equivalents to 4 equivalents, or 2 equivalents to 3 equivalents, with respect to the phosphorus-based catalyst. The water including the acid component is fed to the extraction device 300 in the above content, such that the phosphorus-based catalyst may be efficiently oxidized.

In the oxidizing of the phosphorus-based catalyst by feeding water including an acid component to the extraction device to inactivate the phosphorus-based catalyst, the water including the acid component may include, for example, one or more selected from the group consisting of a hydrochloric acid aqueous solution, a sulfuric acid aqueous solution, and a nitric acid aqueous solution. As a specific example, in the present invention, the water including the acid component may be a hydrochloric acid aqueous solution.

The water including the acid component may be separated from the extraction device 300 and discharged, and the discharged water including the acid component may be re-circulated to the extraction device 300.

The oxidized and inactivated phosphorus-based catalyst may be represented by Formula 2.

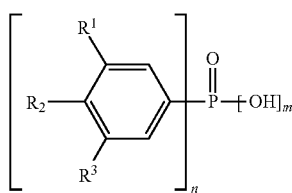

[Formula 2]

In Formula 2, each of $R_1$ to $R_3$ represents hydrogen, or an alkyl group, amine group, or alkoxy group having 1 to 5 carbon atoms, and n and m are each independently an integer of 1 or 2.

As a specific example, the oxidized phosphorus-based catalyst may be represented by Formula 2, and in this case, each of $R_1$ and $R_3$ may be hydrogen, and $R_2$ may be hydrogen, a methyl group, or an ethyl group.

As such, the oxidized and inactivated phosphorus-based catalyst may be in a solid state. As such, the inactivated phosphorus-based catalyst in the solid state may be separated by a simple method using a filter. For example, the filter may be a filtration net, and the filtration net may have a mesh size capable of filtering the inactivated phosphorus-based catalyst in the solid state, such that a the inactivated phosphorus-based catalyst in the solid state may be filtered and separated from the liquid material.

According to an exemplary embodiment of the present invention, the inactivated phosphorus-based catalyst may be reused as a catalyst for the acrylonitrile dimerization reaction in the dimerization reactor 100 through a separate activation step.

For example, in the activation step, the inactivated phosphorus-based catalyst represented by Formula 2 is reacted with an inorganic phosphorus halide compound to convert the inactivated phosphorus-based catalyst into a compound represented by Formula 3 which is an intermediate capable of synthesizing the phosphorus-based catalyst represented by Formula 1, and then the compound is reacted with the alcohol solvent, such that the compound may be activated as the phosphorus-based catalyst represented by Formula 1 again.

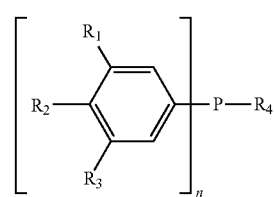

[Formula 3]

In Formula 3, each of $R_1$ to $R_3$ represents hydrogen, or an alkyl group, amine group, or alkoxy group having 1 to 5 carbon atoms, $R_4$ represents a halogen element, and n is an integer of 1 or 2.

As a specific example, the compound which is the intermediate may be represented by Formula 3, and in this case, each of $R_1$ and $R_3$ may be hydrogen, $R_2$ may be hydrogen, a methyl group, or an ethyl group, and $R_4$ may be chlorine (Cl), but the present invention is not limited thereto.

As a more specific example, the inorganic phosphorus halide may be $PCl_3$, and the alcohol solvent may include one or more selected from the group consisting of isopropyl alcohol, methyl alcohol, and cyclohexane alcohol, but the present invention is not limited thereto.

According to an exemplary embodiment of the present invention, a separate distillation column (not illustrated) may be provided to separate respective components of the acrylonitrile dimer and the nonpolar solvent which are residual components obtained by separating the inactivated phosphorus-based catalyst from the extraction device 300. Specifically, the acrylonitrile dimer is separated and recovered from the separate distillation column (not illustrated), and the nonpolar solvent is separated to be circulated to the dimerization reactor 100, such that the nonpolar solvent may be involved in the acrylonitrile dimerization reaction again.

The acrylonitrile dimer separated and recovered from the distillation column (not illustrated) may include one or more selected from the group consisting of 1,4-dicyanobutene and 2-methyleneglutaronitrile.

Purity of the acrylonitrile dimer separated and recovered from the distillation column (not illustrated) may be 95% or more. For example, the purity of the acrylonitrile dimer separated and recovered from the distillation column (not illustrated) may be 70% to 100%, 75% to 100%, or 80% to 100%. As such, the catalyst used in the dimerization reaction of acrylonitrile is efficiently separated by the method according to the present invention, such that an acrylonitrile dimer may be produced at a high purity.

According to an exemplary embodiment of the present invention, in the method of producing an acrylonitrile dimer, a distillation column (not illustrated), a condenser (not illustrated), a reboiler (not illustrated), a pump (not illustrated), a compressor (not illustrated), a mixer (not illustrated), and a separator (not illustrated) may be additionally installed, if necessary.

Hereinabove, the method of producing an acrylonitrile dimer according to the present invention has been described and illustrated in the drawing. However, the description and the illustration of the drawing are for only essential components for understating the present invention, and processes and apparatuses not separately described and illustrated may be properly applicable and used for implementing the method of producing an acrylonitrile dimer, in addition to the processes and apparatuses described and illustrated in the drawing.

Hereinafter, the present invention will be described in more detail by examples. However, the following examples are provided for illustrating the present invention. It is apparent to those skilled in the art that various modifications and alterations may be made without departing from the scope and spirit of the present invention, and the scope of the present invention is not limited thereto.

EXAMPLES

Example 1

As in the process flow diagram illustrated in FIG. 1, 3 mL of an acrylonitrile monomer (AN), 10 mL of a toluene solvent (Tol), 1 mL of isopropyl alcohol (ROH), and a phosphorus-based catalyst of Formula 1-2 were fed to a dimerization reactor 100 at 5 mol % with respect to AN, and an acrylonitrile dimerization reaction was performed under conditions of normal pressure and a temperature of 60° C.

[Formula 1-2]

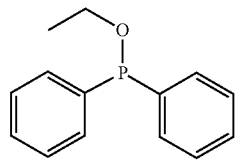

In this case, the catalyst, the monomer, and the solvent used in the acrylonitrile dimerization reaction are shown in Table 1.

TABLE 1

| Type | Use | Manufacturer | Molecular weight (g/mol) | Density (g/mL) | Boiling point (° C.) |
|---|---|---|---|---|---|
| Ethyl diphenyl-phosphinite (97%) | Phosphorus-based catalyst | Sigma-Aldrich | 230.25 | 1.07 | 152 |
| Acrylonitrile | Monomer | Sigma-Aldrich | 53.064 | 0.81 | 77 |
| Toluene | Solvent | Sigma-Aldrich | 92.141 | 0.87 | 111 |
| Isopropyl alcohol | Solvent | Sigma-Aldrich | 60.096 | 0.786 | 82.6 |

The acrylonitrile dimerization reaction product subjected to the reaction was fed to a distillation column 200 to partially or entirely re-circulate the acrylonitrile monomer, the isopropyl alcohol, and the toluene to the dimerization reactor 100, and an acrylonitrile dimer, the toluene, and the phosphorus-based catalyst were fed to an extraction device 300 after removing heavies using a filter.

In the extraction device 300, a hydrochloric acid (HCl) aqueous solution (35 to 37 wt %) was separately fed in an amount of 2 equivalents with respect to the phosphorus-based catalyst to oxidize the phosphorus-based catalyst as Formula 2-1, thereby inactivating the phosphorus-based catalyst. In this case, the hydrochloric acid aqueous solution was circulated to the extraction device 300, and as a result of measuring a conversion rate of converting the phosphorus-based catalyst represented by Formula 1-2 into Formula 2-1 obtained by analysis with a gas chromatography (GC)/flame ionization detector (FID) (Shidmadz GC-2030), it was confirmed that the conversion rate was 70% or more.

[Formula 2-1]

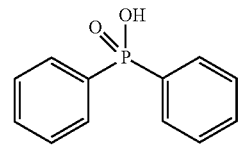 [SMILES: O=P(O)(c1ccccc1)c1ccccc1]

In this case, the GC/FID analysis condition is as shown in Table 2.

TABLE 2

| | |
|---|---|
| Injection type | Split (ratio: 45.6) |
| Injector temperature | 260° C. |
| Carrier gas | N₂ (Total flow: 42.4 mL/min) |
| Column | HP-5MS (0.25 mm ID × 30.0 mL, 0.25 μm FT) |
| Oven temperature | 100° C., 3 min |
| Rate | 40° C. to 130° C. (15° C./min), 135° C. to 280° C. (5° C./min) |
| Detector temperature | 350° C., FID |
| Injection volume | 1 μl |

Then, the solid inactivated phosphorus-based catalyst was separated using a filter, and the acrylonitrile dimer was separated from a mixture of the acrylonitrile dimer and the toluene, thereby obtaining 1,4-dicyanobutene (DCB) and 2-methyleneglutaronitrile (MGN) as final products.

Comparative Example 1

Comparative Example 1 was performed in the same manner as that of Example 1, except that the acrylonitrile dimerization reaction product subjected to the reaction was not fed to the distillation column 200, that is, the process of separating the isopropyl alcohol from the acrylonitrile dimerization reaction product subjected to the reaction was not performed, the heavies were removed from the mixture in which the acrylonitrile dimer, the toluene, the isopropyl alcohol, and the phosphorus-based catalyst were mixed with each other using a filter, and the mixture was fed to the extraction device 300 in Example 1.

To the extraction device 300 to which the mixture from which the heavies were removed was fed, a hydrochloric acid (HCl) aqueous solution (35 to 37 wt %) was separately fed in an amount of 2 equivalents with respect to the phosphorus-based catalyst to oxidize the phosphorus-based catalyst as Formula 2-1, thereby inactivating the phosphorus-based catalyst.

In this case, the oxidized, inactivated, and solidified phosphorus-based catalyst as Formula 2-1 was re-dissolved in the isopropyl alcohol present in the mixture, and the phosphorus-based catalyst was not separated as a phosphorus-based catalyst in a solid state.

As such, it was confirmed that in a case where the phosphorus-based catalyst was solidified by adding the hydrochloric acid aqueous solution (that is, water including an acid) to the reaction product in which the alcohol solvent was not preferentially separated, the solidified phosphorus-based catalyst was re-dissolved in the alcohol solvent and thus was not recovered in a solid state.

The invention claimed is:
1. A method of producing an acrylonitrile dimer, the method comprising:

feeding an acrylonitrile monomer, a nonpolar solvent, an alcohol solvent, and a phosphorus-based catalyst to a dimerization reactor to perform a dimerization reaction and feeding a reaction product to a distillation column;

feeding the acrylonitrile monomer, the nonpolar solvent, and the alcohol solvent partially or entirely separated from the distillation column to the dimerization reactor;

and feeding an acrylonitrile dimer and the phosphorus-based catalyst separated from the distillation column to an extraction device;

oxidizing the phosphorus-based catalyst by feeding water including an acid component to the extraction device to inactivate the phosphorus-based catalyst; and separating the inactivated phosphorus-based catalyst and the acrylonitrile dimer.

2. The method of claim 1, wherein the phosphorus-based catalyst is represented by Formula 1:

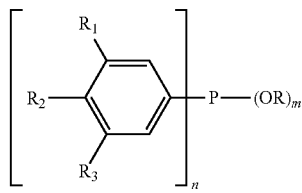

[Formula 1]

in Formula 1,

R represents an alkyl group having 1 to 5 carbon atoms or a cycloalkyl group having 1 to 8 carbon atoms, each of $R_1$ to $R_3$ represents hydrogen, or an alkyl group, amine group, or alkoxy group having 1 to 5 carbon atoms, and n and m are each independently an integer of 1 or 2.

3. The method of claim 1, wherein a content of the alcohol solvent in the extraction device is 1 wt % or less.

4. The method of claim 1, wherein a content of the nonpolar solvent in the extraction device is 5 wt % or less.

5. The method of claim 1, wherein the water including the acid component is fed in an amount of 2 equivalents or more with respect to the phosphorus-based catalyst.

6. The method of claim 1, wherein in the oxidizing of the phosphorus-based catalyst by feeding water including an acid component to the extraction device to inactivate the phosphorus-based catalyst, the water including the acid component includes one or more selected from the group consisting of a hydrochloric acid aqueous solution, a sulfuric acid aqueous solution, and a nitric acid aqueous solution.

7. The method of claim 1, wherein the inactivated phosphorus-based catalyst is represented by Formula 2:

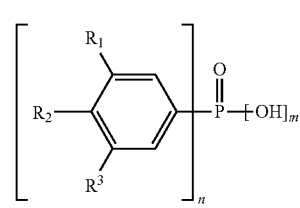

[Formula 2]

in Formula 2, each of $R_1$ to $R_3$ represents hydrogen, or an alkyl group, amine group, or alkoxy group having 1 to 5 carbon atoms, and n and m are each independently an integer of 1 or 2.

8. The method of claim 1, wherein the inactivated phosphorus-based catalyst is a solid.

9. The method of claim 1, wherein the separating of the inactivated phosphorus-based catalyst and the acrylonitrile dimer is performed using a filter.

10. The method of claim 1, wherein the separated phosphorus-based catalyst is reused in the dimerization reactor.

11. The method of claim 1, wherein in the distillation column, an operation temperature is 40° C. to 150° C., and an operation pressure is 0.001 bar to 3 bar.

12. The method of claim 2, wherein in Formula 1, R represents an ethyl group, each of $R_1$ to $R_3$ represents hydrogen, and n is 2 and m is 1.

13. The method of claim 7, wherein in Formula 2, each of $R_1$ to $R_3$ represents hydrogen, and n is 2 and m is 1.

* * * * *